United States Patent [19]

Treuner et al.

[11] 4,124,764
[45] Nov. 7, 1978

[54] MESO-IONIC DIDEHYDRO DERIVATIVES OF 1,7-DEHYDRO-1-SUBSTITUTED-3H-PYRAZOLO[4,3-E]-1,2,4-TRIAZOLO[4,3-C]PYRIMIDINE-3-THIONES AND 3-ONES

[75] Inventors: Uwe D. Treuner; Hermann Breuer, both of Regensburg, Germany

[73] Assignee: E. R. Squibb & Sons, Inc., Princeton, N.J.

[21] Appl. No.: 833,103

[22] Filed: Sep. 13, 1977

Related U.S. Application Data

[63] Continuation-in-part of Ser. No. 678,832, Apr. 21, 1976, Pat. No. 4,053,474.

[51] Int. Cl.$^2$ ................ A61K 31/505; C07D 487/14
[52] U.S. Cl. .................................. 544/251; 544/263; 424/251
[58] Field of Search ............... 544/251; 260/256.4 F, 260/256.5 R

[56] References Cited

U.S. PATENT DOCUMENTS

| | | | |
|---|---|---|---|
| 3,850,932 | 11/1974 | Kathawala | 260/256.4 F |
| 4,020,083 | 4/1977 | Kathawala | 260/256.4 F |
| 4,026,893 | 5/1977 | Denzel et al. | 260/256.4 F |
| 8,787,430 | 1/1974 | Hoehen et al. | 260/296 H |

OTHER PUBLICATIONS

Reimlinger, et al., "Chem. Ber.", vol. 103 (1970), pp. 1960–1981.
Sihdu et al., "Die Naturwissenschaften", vol. 732 (1963).
"Derwent Patent Abstracts", 77971T-BE(1973).

*Primary Examiner*—Donald G. Daus
*Assistant Examiner*—James H. Turnipseed
*Attorney, Agent, or Firm*—Lawrence S. Levinson; Merle J. Smith

[57] ABSTRACT

New 1,7-dihydro-1-substituted-3H-pyrazolo[4,3-e]-1,2,4-triazolo[4,3-c]pyrimidine-3-thione and 3-one mesoionic didehydro derivatives which have the formula

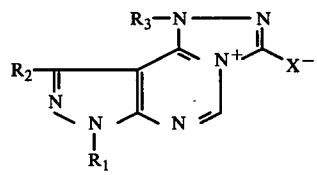

wherein
$R_1$ is hydrogen, lower alkyl, phenyl-lower alkyl, cycloalkyl or hydroxy-lower alkyl;
$R_2$ is hydrogen or lower alkyl;
$R_3$ is lower alkyl, cycloalkyl or hydroxy-lower alkyl; and
X is sulfur or oxygen,
are useful as anti-inflammatory agents.

12 Claims, No Drawings

MESO-IONIC DIDEHYDRO DERIVATIVES OF 1,7-DEHYDRO-1-SUBSTITUTED-3H-PYRAZOLO[4,3-E]-1,2,4-TRIAZOLO[4,3-C]PYRIMIDINE-3-THIONES AND 3-ONES

This application is a continuation-in-part of our copending application Ser. No. 678,832, filed Apr. 21, 1976, U.S. Pat. No. 4,053,474, October 11, 1977.

BACKGROUND OF THE INVENTION

Our earlier application Ser. No. 678,832, filed Apr. 21, 1976, describes a group of 3-mercapto-7H-pyrazolo-[4,3-e]-1,2,4-triazolo[4,3-c]pyrimidines unsubstituted or lower alkyl substituted in the 7- and/or 9-positions as well as derivatives in which the sulfur in the 3-position bears various substituents. These previously described compounds are obtained, according to one method, from a 1-and/or 3- unsubstituted or substituted 4-halopyrazolo[3,4-d]pyrimidine by sequential treatment with hydrazine and 1,1-thiocarbonyl diimidazole.

It has now been found that treatment of the same unsubstituted or substituted 4-halopyrazolo[3,4-d]pyrimidine with a monosubstituted hydrazine instead of hydrazine and then with 1,1-thiocarbonyldiimidazole yields a 1,7-dihydro-1- substituted -3H-pyrazolo[4,3-e]-1,2,4-triazolo[4,3-c]pyrimidine- 3-thinoe meso-ionic didehydro derivative, an inner salt or meso-ionic form in which the sulfer has a negative charge and a nitrogen has a positive charge, and the substituent on the original hydrazine reactant is now in the 1 -position. The same meso-ionic derivatives can also be obtained by utilizing carbon disulfide instead of 1,1 -thiocarbonyldiimidazole. Similarly, when 1,1-carbonyldiimidazole is used instead of 1,1- thiocarbonyldiimidazole, the analogous oxygen containing products are obtained.

SUMMARY OF THE INVENTION

This invention relates to new 1,7-dihydro-1-substituted- 3H-pyrazolo[4,3-e]-1,2,4-triazolo[4,3-c]pyrimidine-3-thione or 3-one meso-ionic didehydro derivatives which have the general formula

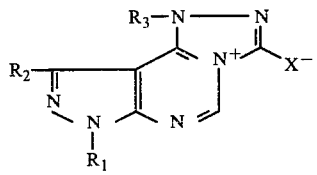

wherein
$R_1$ is hydrogen, lower alkyl, phenyl-lower alkyl, hydroxy-lower alkyl or cyclo-lower alkyl;
$R_2$ is hydrogen or lower alkyl;
$R_3$ is lower alkyl, cyclo-lower alkyl or hydroxy-lower alkyl; and
X is sulfur or oxygen.

DETAILED DESCRIPTION OF THE INVENTION

The lower alkyl groups represented by $R_1$, $R_2$ and $R_3$ are straight or branched chain aliphatic hydrocarbon radicals having up to seven carbon atoms. The $C_1$-$C_4$ members, and especially the $C_{1-C2}$ members are preferred. Illustrative lower alkyl groups are methyl, ethyl, propyl, isopropyl, butyl, isobutyl, t-butyl, amyl and the like.

The hydroxy-lower alkyl groups are similar groups bearing a hydroxy substituent, preferably on the terminal carbon, e.g., hydroxymethyl, 2-hydroxyethyl, 3-hydroxypropyl and the like. The same preferences as above apply.

Similarly, the phenyl-lower alkyl groups include a phenyl substituent on the alkyl chain, preferably on a terminal carbon. Again, these groups having one to four carbons in the alkyl chain, especially one or two as in phenylmethyl and phenylethyl, are preferred. The cyclo-lower alkyl groups similarly have up to seven carbon, preferably $C_5$-$C_6$.

Preferred are compounds of Formula I wherein $R_1$ and $R_3$ *each is lower alkyl, especially* $C_1$-$C_4$ alkyl, and $R_2$ is hydrogen, most especially when X is sulfer. The examples illustrate particularly preferred embodiments The products of this invention are synthesized from a 4-halopurazolo[3,4-d]pyrimidine which has the formula

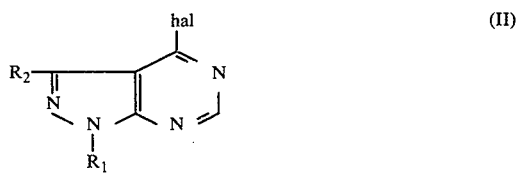

wherein hal represents halogen, preferably chlorine.

The 4-halopyrazolo[3,4-d]pyrimidine is first made to react with a substituted hydrazine which has the formula

In an alcohol like ethanol or propanol, preferably at about ambient temperature. This reaction results in an intermediate which has the formula

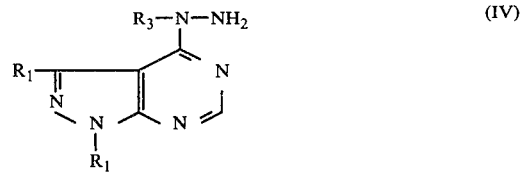

When the intermediate of formula IV is then made to react with 1,1-thiocarbonyldiimidazole or with carbon disulfide in an inert organic reaction medium like dimethylformamide, ethyl acetate, diglyme or the like, preferably at an elevated temperature, e.g., about 80° C., a product of formula I wherein X is sulfer is obtained. When 1,1-carbonyldiimidazole is used instead, a product of formula I wherein X is oxygen is obtained.

When $R_1$ is hydrogen or hydroxy-lower alkyl, the 1-position or the hydroxy function, respectively, should be protected, e.g., as in U.S. Pat. 3,828,057, prior to reaction with the diimidazole and finially deprotected.

The starting materials can be produced by the methods described in our aforementioned copending application, in U.S. Pat. Nos. 3,720,674, issued Mar. 13, 1973, 3,723,225, issued May 8, 1973 and 3,873,556, issued Mar. 25, 1975, and J. Org. Chem 21, 1240 (1956).

The new compounds of this invention have anti-inflammatory properties and are useful as anti-inflammatory agents, for example, to reduce local inflammatory conditions such as those of an edamatous nature or resulting from proliferation of connective tissue in various mammalian species such as rats, dogs and the like when given orally in dosages of about 1 to 100 mg/kg/day, preferably 3 to 20 mg/kg/day, in single or 2 to 4 divided doses, as indicated by the Mouse Active Arthus Assay. The active substance is formulated in a composition such as tablet, capsule, solution or suspension containing up to about 500 mg. per unit of dosage of a compound or mixture of compounds of formula I. The material is compounded in conventional manner with a physiologically acceptable vehicle or carrier, excipeient, binder, preservative, stabilizer, flavor, etc., as called for by accepted pharmaceutical practice. Topical preparations containing about 0.01 to 3 percent by weight of active substance in a conventional lotion, cream or ointment can also be used.

The following examples are illustrative of the invention and serve as models for the production of additional members by replacing with the appropriately substituted reactants. All temperatures are in degrees Celsius.

EXAMPLE 1

1,7-Dihydro-1,7-dimethyl-3H-pyrazolo[4,3-e]-1,2,4-triazolo-[4,3-c]pyrimidine-3-thione meso-ionic didehydro derivative (a) 1-methyl-4-carboethyoxy-5-aminopyrazole 320g. of ethoxymethylene cyanoacetic acid ester are dissolved in 2 liters of absolute ethanol. 87 g. of methylhydrazine are added dropwise with stirring. The temperature rises to 35°. The reaction mixture is then refluxed for 12 hours. After distilling off the solvent, the solid residue is crystallized from a little methanol to obtain 162 g. (95.8%) of 1-methyl-4-carboethoxy-5-aminopyrazole, m.p. 92°–93°. (b) 5-[(Ethoxymethylene)amino]-1-methyl-1H-pyrazole-4-carboxylic acid, ethyl ester 84.6 g. of 1-methyl-4-carboethoxy-5-aminopyrazole and 74.1 g. of orthoformic acid triethyul ester are heated together until the splitting off of ethanol has ended. The oily residue is distilled under oil pump vacuum to obtain 5-[(ethoxy-methylene)amino]-1-methyl-1h-pyrazole-4-carboxylic acid, ethyl ester b.p. 98°–102°; m.p. 32°–34° (yield87%).

(c) 1-Methyl-1,5-dihydro-4H-pyrazolo[3,4-d]pyrimidin-4-one 57.2 g. of 5 -[(ethoxymethylene)amino]-1-methyl-1H-pyrazole-4-carboxylic acid, ethyl ester are dissolved in 200 ml. of ethanol, 4.4 g. of ammonia are added and the reaction mixture is autoclaved at 60° for 40 hours. After cooling, the mixture is filtered and the residual 1-methyl-1,5-dihydro-4H-pyrazolo- [3,4-d]pyrimidin-4-one is crystallized from dimethylformamide, m.p. 289°-290° (yield 31 g. - 80.7%).

(d) 1-Methyl-4-chloropyrazolo[3,4-d]pyrimidine 80 g. of 1-methyl-1,5-dihydro-4H-pyrazolo[3,4-d]-pyrimidin-4-one are added to 300 ml. of phosphorus oxychloride and the mixture is refluxed. After distilling off the excess phosphorus oxychloride, the semi-solid residue is extracted with 3 × 100 ml. of boiling benzene. The benzene extracts are combined and concentrated to half-volume, then added to petroleum ether. After standing 12 hours in the refrigerator, the precipitated 1-methyl-4-chloropyrazolo[3,4-d]- pyrimidine is filtered under suction and recrystallized from cyclohexane to obtain 54 g. of white crystals, m.p. 93°–96° (yield 60.5%).

(e) 1-Methyl-b 4-(1-methylhydrazino)pyrazolo[3,4-d]pyrimidine 81 g. of 1-methyl-4-chloropyrozolo[3,4-d]pyrimidine are dissolved in 1 liter of n-propanol. 45 g. of methylhydrazine are added dropwise at room temperature and stirred for 35 hours. The reaction mixture is filtered and the residual 1-methyl-4-(1-methylhydrazino)-pyrazolo[3,4-d]pyrimidine is recrystallized twice from dimethylformamide having added activated charcoal to obtain 67.2 g. of white crystalline product, m.p. 214° (yield 84%).

(f) 1,7-Dihydro-1,7-dimethyl-3H-pyrazolo[4,3-e]-1,2,4-triazolo- [4,3-c]pyrimidine-3-thione meso-ionic didehydro derivative 31 g. of 1-methyl-4-(1-methylhydrazino)pyrazolo[3,4-d]- pyrimidine are dissolved in 100 ml. of dimethylformamide and 30 g. of 1,1-thiocarbonyldiimidazole dissolved in 20 ml. of dimethylformamide are added all at once. The reaction mixture is stirred for 12 hours at room temperature. The precipitate is filtered under suction and together with the residue, obtained by concentrating the filtrate, crystallized from dimethylformamide having added activated charcoal. 29 g. of 1,7-dihydro-1,7-dimethyl-3H-pyrazolo[4,3-e]-1,2,4-triazolo- [4,3-c]pyrimidine-3-thione meso-ionic didehydro derivative are obtained as yellowish felt-like crystals, m.p. >270° (yield 75.4%).

EXAMPLE 2

1,7-Dihydro-1-methyl-7-methylethyl-3H-pyrazolo[4,3-e]-1,2,4- triazolo[4,3-c]pyrimidine-3-thione meso-ionic didehydro derivative (a) 1-methylethyl-4-carboethoxy-5-aminopyrazole By substituting isopropylhydrazine for the methylhydrazine in the procedure of Example 1a, 1-methylethyl-4-carboethoxy-5-aminopyrazole b.p.$_{0.05mm}$ 123°–127°, is obtained.

(b) 5-[(Ethoxymethylene)amino]-1-(methylethyl)-1H-pyrazole- 4-carboxylic acid, ethyl ester By substituting the product of part a in the procedure of Example 1 (b), b 5-[(ethoxymethylene)amino]-1-(methylethyl)- 1H-pyrazole-4-carboxylic acid, ethyl ester, b.p.$_{0.01}$ 98°–103°, is obtained.

(c) 1-Isopropyl-1,5-dihydro-4H-pryazolo[3,4-d]pyrimidine-4-one

By substituting the product of part b in the procedure of Example 1(c), 1-isopropyl-1,5-dihydro-4H-pyrazolo[3,4-d]- pyrimidine-4-one, m.p. 193°, is obtained.

(d) 4-Chloro-1-methylethylpyrazolo[3,4-d]pyrimidine

By substituting the product of part (c) in the procedure of Example 1(d), 4-chloro-1-methylethyl-pyrazolo[3,4-d]pyrimidine, m.p. 47°–49°, is obtained.

(e)
1-(Methylethyl)-4-(1-methylhydrazino)pyrazolo[3,4-d]pyrimidine

By substituting the product of part (d) in the procedure of Example 1(e), 1-(methylethyl)-4-(1-methylhydrazino)- pyrazolo[3,4-d]pyrimidine, m.p. 105°–108°, is obtained.

(f)
1,7-Dihydro-1-methyl-7-methylethyl-3H-pyrazolo[4,3-e]- 1,2,4-triazolo[4,3-c]pyrimidine-3-thione meso-ionic didehydro derivative By substituting the product of part e in the procedure of Example 1(f), 1,7-dihydro-1methyl-7-methylethyl-3H- pyrazolo[4,3-e]-1,2,4-triazolo[4,3-c]pyrimidine-3-thione meso-ionic didehydro derivative, m.p. 290-292°, is obtained.

EXAMPLE 3

1-Butyl-1,7-dihydro-7-methyl-3H-pyrazolo[4,3-e]-1,2,4-triazolo [4,3-c]pyrimidine-3-thione meso-ionic didehydro derivative (a) 4-(1-Butylhydrazino)-1 methyl-1H-pyrazolo[3,4-d]pyrimidine By substituting butylhydrazine for the methylhydrazine in the procedure of Example 1(e), 4-(1-butylhydrazino)-1-methyl-1H-pyrazolo[3,4-d]pyrimidine, m.p. 68°–72°, is obtained.

(b)
1-Butyl-1,7-dihydro-7-methyl-3H-pyrazolo[4,3-e]-1,2,4-triazolo[4,3-c]pyrimidine-3-thione meso-ionic didehydro derivative By substituting the product of part $a$ in the procedure of Example 1(f), 1-butyl-1,7-dihydro-7-methyl-3H-pyrazolo[4,3-e]-1,2,4-triazolo[4,3-c]pyrimidine-3l -thione meso-ionic didehydro derivative, m.p. 272°–275°, is obtained.

EXAMPLE 4

1,7-Dihydro-1-methylethyl-7-methyl-3H-pyrazolo[4,3-e]-1,2,4-triazolo[4,3-c]pyrimidine-3-thione meso-ionic didehydro derivative (a)
4-(1-Methylethylhydrazino)-1-methyl-1H-pyrazolo[3,4-d]pyrimidine By substituting isopropylhydrazine for the methylhydrazine in the procedure of Example 1(e), 4-(1-methylethylhydrazino)-1-methyl-1H-pyrazolo[3,4-d]pyrimidine, m.p. 57°, is obtained.

(b)
1,7-Dihydro-1-methylethyl-7-methyl-3H-pyrazolo[4,3-e]-1,2,4-triazolo[4,3-c]pyrimidine-3-thione meso-ionic didehydro derivative By substituting the product of part $a$ in the procedure of Example 1(f), 1,7-dihydro-1-methylethyl-7-methyl-3H-pyrazolo[4,3-e]-1,2,4-triazolo[4,3-c]pyrimidine-3-thione meso-ionic didehydro derivative, m.p. 316°–317°, is obtained.

EXAMPLE 5

1,7-Dihydro-1,7-dimethyl-3H-pyrazolo[4,3-e]-1,2,4-triazolo[4,3-c]pyrimidine-3-thione meso-ionic didehydro derivative (a)
1-Methyl-4-(1-methylhydrazino)pyrazolo[3,4-d]pyrimidine 1.7 g. of methylhydrazine is dissolved in 30 ml. of ethanol. 3.3 g. of 4-chloro-1-methylpyrazolo[3,4-d]pyrimidine is added portionwise. The mixture is refluxed for 30 minutes and then allowed to stand in the refrigerator overnight. The mixture is filtered and the product, 1-methyl-4-(1-methylhydrazino)pyrazolo[3,4-d]pyrimidine, is recrystallized from ethanol-methanol, m.p. 213°–215° (yield 4.2 g.).

(b)
1,7-Dihydro-1,7-dimethyl-3H-pyrazolo[4,3-e]-1,2,4-triazolo[4,3-c]pyrimidine-3-thione meso-ionic didehydro derivative 0.5 g. of the prodcut of part $a$ is dissolved in 10 ml. of dimethylformamide. 0.22 g. of carbon disulfide is added dropwise. The reaction mixture is then heated at 80° for 2 hours. The product, 1,7-dihydro-1,7-dimethyl-3H-pyrazolo[4,3-e]-1,2,4-triazolo[4,3-c]pyrimidine-3-thione meso-ionic didehydro derivative, crystallizes during the course of the reaction. The reaction mixture is cooled and filtered to obtain 0.5 g. of the product, m.p. 300°.

EXAMPLE 6

1,7-Dihydro-1,7-dimethyl-3H-pyrazolo[4,3-e]-1,2,4-triazolo[4,3-c]pyrimidine-3-one meso-ionic didehydro derivative 1.7 g. of 1-methyl-4-(1-methylhydrazino)-pyrazolo[3,4-d]pyrimidine and 1.62 g. of 1,1-carbonyldiimidazole in 20 ml. of dimethylformamide are stirred at 80° for several minutes. The product, 1,7-dihydro-1,7-dimethyl-3H-pyrazolo[4,3-e]-1,2,4-triazolo[4,3-c]pyrimidine-3-one-meso-ionic didehydro derivative, precipitates in the form of felt-like needles. The product is recrystallized from dimethylformamide, m.p. 303°–306° (yield 1.6g.).

The following additional compounds are produced by the procedure of Example 1 by forming the appropriately ($R_1$ and $R_2$) substituted aminopyrazole (according to parts $a$ and $b$), and utilizing the appropriately ($R_3$) substituted hydrazine (according to part $e$), (and Example 6 instead of Example 1(f) for compounds wherein X is oxygen).

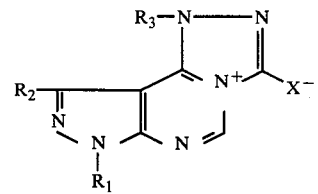

| Ex. | $R_1$ | $R_2$ | $R_3$ | X |
|---|---|---|---|---|
| 7 | $CH_3$— | $CH_3$— | $C_2H_5$— | S |
| 8 | $C_2H_5$— | $C_2H_5$— | $CH_3$— | S |
| 9 | H | H | $CH_3$— | S |
| 10 | H | $C_2H_5$— | $HOCH_2CH_2$— | S |
| 11 | $HOCH_2CH_2$— | H | $CH_3$ | S |
| 12 | $HOCH_2CH_2$— | H | $HOCH_2CH_2$— | S |
| 13 | $C_2H_5$— | $CH_3$— | $C_2H_5$— | O |
| 14 | H | H | $CH_3$— | O |
| 15 | H | $CH_3$— | $HOCH_2CH_2$— | O |

-continued

[Structure: pyrazolo-triazolo fused ring system with R1, R2, R3, X substituents]

| Ex. | R1 | R2 | R3 | X |
|-----|----|----|----|---|
| 16 | HOCH₂CH₂— | H | HOCH₂CH₂— | O |
| 17 | CH₃ | H | HOCH₂CH₂— | O |
| 18 | C₆H₅-CH₂— | H | C₃H₇— | O |
| 19 | C₆H₅-CH₂CH₂— | H | C₄H₉— | S |
| 20 | (tetrahydrothiopyranyl) | H | CH₃ | O |
| 21 | (tetrahydrothiopyranyl) | H | C₂H₅ | O |
| 22 | (tetrahydrothiophenyl) | H | CH₃ | O |
| 23 | C₂H₅ | H | (tetrahydrothiopyranyl) | O |
| 24 | (tetrahydrothiopyranyl) | H | CH₃ | S |

What is claimed is:

1. A compound of the formula

[Structure diagram]

wherein
$R_1$ is hydrogen, lower alkyl, phenyl-lower alkyl, cyclo-lower alkyl or monohydroxy-lower alkyl;
$R_2$ is hydrogen or lower alkyl;
$R_3$ is lower alkyl, cyclo-lower alkyl or monohydroxy-lower alkyl; and
X is sulfur or oxygen.

2. A compound as in claim 1 wherein $R_2$ is hydrogen.
3. A compound as in claim 1 wherein $R_1$ is lower alkyl and $R_2$ is hydrogen.
4. A compound as in claim 1 wherein X is sulfur.
5. A compound as in claim 1 wherein X is oxygen.
6. A compound as in claim 4 wherein $R_1$ and $R_3$ each is lower alkyl and $R_2$ is hydrogen.
7. A compound as in claim 5 wherein $R_1$ and $R_3$ each is lower alkyl and $R_2$ is hydrogen.
8. A compound as in claim 4 wherein $R_1$ and $R_3$ each is methyl and $R_2$ is hydrogen.
9. A compound as in claim 4 wherein $R_1$ is methyl, $R_2$ is hydrogen and $R_3$ is methylethyl.
10. A compound as in claim 4 wherein $R_1$ is methylethyl, $R_2$ is hydrogen and $R_3$ is methyl.
11. A compound as in claim 4 wherein $R_1$ is methyl, $R_2$ is hydrogen and $R_3$ is n-butyl.
12. A compound as in claim 5 wherein $R_1$ and $R_3$ each is methyl and $R_2$ is hydrogen.

* * * * *